US008955970B2

(12) United States Patent
Nozato

(10) Patent No.: US 8,955,970 B2
(45) Date of Patent: Feb. 17, 2015

(54) FUNDUS IMAGING METHOD, FUNDUS IMAGING APPARATUS, AND STORAGE MEDIUM

(75) Inventor: Koji Nozato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 104 days.

(21) Appl. No.: 13/309,841

(22) Filed: Dec. 2, 2011

(65) Prior Publication Data

US 2012/0154746 A1 Jun. 21, 2012

(30) Foreign Application Priority Data

Dec. 20, 2010 (JP) ................................ 2010-283728

(51) Int. Cl.
*A61B 3/10* (2006.01)
*A61B 3/14* (2006.01)
*A61B 3/12* (2006.01)

(52) U.S. Cl.
CPC ................ *A61B 3/12* (2013.01); *A61B 3/1015* (2013.01)
USPC ......................................... 351/206; 351/205

(58) Field of Classification Search
USPC .................... 351/205, 206, 221, 246
See application file for complete search history.

(56) References Cited

U.S. PATENT DOCUMENTS

| 7,520,613 | B2 | 4/2009 | Saito et al. |
| 7,537,341 | B2 | 5/2009 | Saito et al. |
| 2008/0218694 | A1 | 9/2008 | Chen et al. |
| 2008/0225228 | A1 | 9/2008 | Saito et al. |
| 2008/0225230 | A1 | 9/2008 | Saito et al. |
| 2010/0097572 | A1* | 4/2010 | Nakanishi et al. ............ 351/205 |
| 2010/0166293 | A1 | 7/2010 | Sugita et al. |
| 2012/0019780 | A1 | 1/2012 | Nozato |
| 2012/0169998 | A1* | 7/2012 | Lai ................................ 351/241 |

FOREIGN PATENT DOCUMENTS

| CN | 1245406 A | 2/2000 |
| CN | 101869466 A | 10/2010 |
| JP | 2004-059779 A | 2/2004 |
| JP | 2004-113405 A | 4/2004 |
| JP | 2008-220770 A | 9/2008 |
| JP | 2008-220771 A | 9/2008 |

OTHER PUBLICATIONS

Apr. 12, 2012 European Search Report in European Patent Appln. No. 11009434.9.

(Continued)

*Primary Examiner* — Mahidere Sahle
(74) *Attorney, Agent, or Firm* — Fitzpatrick, Cella, Harper & Scinto

(57) ABSTRACT

A fundus imaging apparatus includes: an aberration measurement unit adapted to measure an aberration of reflected light obtained by irradiating an object to be examined with measurement light; an aberration correction unit adapted to correct an aberration of light in accordance with the measured aberration; a control unit adapted to repeatedly control processing of the aberration measurement unit and the aberration correction unit; and a changing unit adapted to change a first function of a predetermined order representing the aberration to a second function including an order higher than the predetermined order in accordance with at least one of a measurement result obtained by the aberration measurement unit and a control result obtained by the control unit. The aberration correction unit corrects an aberration expressed by the second function.

16 Claims, 9 Drawing Sheets

(56) References Cited

OTHER PUBLICATIONS

Y. Zhang et al., "High-speed volumetric imaging of cone photoreceptors with adaptive optics spectral-domain optical coherence tomography", Optics Express, vol. 14, No. 10, May 15, 2006, pp. 4380-4394.

Jan. 10, 2014 Chinese Official Action in Chinese Patent Appln. No. 201110430451.5.

* cited by examiner

FUNDUS IMAGING METHOD, FUNDUS IMAGING APPARATUS, AND STORAGE MEDIUM

BACKGROUND OF THE INVENTION

1. Field of the Invention

The present invention relates to a fundus imaging method, a fundus imaging apparatus, and a storage medium.

2. Description of the Related Art

Recently, as an ophthalmic imaging apparatus, an SLO (Scanning Laser Ophthalmoscope) has been developed, which two-dimensionally irradiates the fundus with a laser beam, receives reflected light, and images the light. In addition, as an ophthalmic imaging apparatus, an imaging apparatus using low-coherence light interference has been developed. The imaging apparatus using lower-coherence light interference is called an OCT (Optical Coherence Tomography), which is used for the purpose of obtaining a tomogram of the fundus or its neighboring region, in particular. Various types of OCTs have been developed, including a TD-OCT (Time Domain OCT) and an SD-OCT (Spectral Domain OCT). Ophthalmic imaging apparatuses have recently been increased in resolution with increasing NA of irradiation lasers.

When, however, imaging the fundus, it is necessary to perform imaging through optical tissues of the eye, such as the cornea and the crystalline lens. For this reason, with an increase in resolution, the aberrations of the cornea and crystalline lens have started to greatly influence the image quality of captured images.

Under the circumstances, studies have been made on an AO (Adaptive Optics)-SLO and AO-OCT, in which an optical system incorporates an AO function for measuring the aberrations of the eye and correcting them. For example, non-patent literature 1 (Y. Zhang et al, Optics Express, Vol. 14, No. 10, 15 May 2006) discloses an example of an AO-OCT. Such AO-SLO and AO-OCT measure the wavefront of the eye by the Shack-Hartmann wavefront sensor system. The Shack-Hartmann wavefront sensor system is designed to measure the wavefront of the eye by applying measurement light to the eye and making a CCD camera receive the reflected light through a microlens array. An AO-SLO or AO-OCT can perform high-resolution imaging by driving a deformable mirror and a spatial phase modulator so as to correct a measured wavefront and imaging the fundus through them.

Most of the aberrations of the eye are lower-order aberrations, such as myopia, hyperopia, and astigmatism. However, the aberrations also include higher-order aberrations due to the fine recesses and projections on the optical system of the eye and the disturbance of a tear film. When the aberrations of the eye are to be expressed by a Zernike function system, most of the Zernike functions expressing the aberrations are Zernike second-order functions expressing myopia, hyperopia, and astigmatism. These functions slightly include Zernike third-order functions and Zernike fourth-order functions, and more slightly include higher-order functions such as Zernike fifth-order functions and Zernike sixth-order functions.

In general, the adaptive optics (AO) used in an ophthalmic apparatus models an aberration measured by the wavefront sensor with a function such as a Zernike function and calculates a correction amount for a wavefront correction unit by using the function. The amount quantitatively obtained by modeling an aberration with a function will be referred to as an amount of aberration. In addition, a wavefront-correction value with which the wavefront correction unit corrects an aberration by using the function will be referred to as a correction amount. In order to correct a complex shape, it is necessary to model an aberration with a function having many orders, calculate a correction amount, and control the wavefront correction unit.

If, however, a correction amount is calculated by modeling an aberration with a function having many orders, the calculation load becomes very heavy, and the calculation time increases, thus posing a serious problem. For the aberrations of the eye, in particular, it is very important to increase the processing speed because the state of tear and the state of dioptic adjustment always change and aberration correction needs to be repeated fast for the acquisition of a tomogram.

SUMMARY OF THE INVENTION

The present invention has been made in consideration of the above problems and provides a fundus imaging technique capable of performing computation processing for aberration correction at high speed.

According to one aspect of the present invention, there is provided a fundus imaging method for a fundus imaging apparatus including an aberration measurement unit adapted to measure an aberration of reflected light obtained by irradiating an object to be examined with measurement light, an aberration correction unit adapted to correct an aberration of light in accordance with the measured aberration, and a control unit adapted to repeatedly control processing of the aberration measurement unit and the aberration correction unit, the method comprising: a changing step of changing a first function of a predetermined order representing the aberration to a second function including an order higher than the predetermined order in accordance with at least one of a measurement result obtained by the aberration measurement unit and a control result obtained by the control unit; and an aberration correction step of correcting an aberration expressed by the second function.

According to another aspect of the present invention, there is provided a fundus imaging apparatus comprising: an aberration measurement unit adapted to measure an aberration of reflected light obtained by irradiating an object to be examined with measurement light; an aberration correction unit adapted to correct an aberration of light in accordance with the measured aberration; a control unit adapted to repeatedly control processing of the aberration measurement unit and the aberration correction unit; and a changing unit adapted to change a first function of a predetermined order representing the aberration to a second function including an order higher than the predetermined order in accordance with at least one of a measurement result obtained by the aberration measurement unit and a control result obtained by the control unit, wherein the aberration correction unit corrects an aberration expressed by the second function.

According to the present invention, it is possible to perform computation processing for aberration correction at high speed.

Further features of the present invention will become apparent from the following description of exemplary embodiments (with reference to the attached drawings).

DESCRIPTION OF THE EMBODIMENTS

The embodiments of the present invention will be exemplarily described in detail below with reference to the accompanying drawings. The constituent elements described in these embodiments are merely examples, and the technical range of the present invention is defined by the appended claims, but is not limited to each embodiment described below.

First Embodiment

The arrangement of a fundus imaging apparatus according to the first embodiment of the present invention will be described with reference to FIG. 1. Note that this embodiment will exemplify a case in which an object to be examined as a measurement target is an eye, aberrations occurring in the eye are corrected by the adaptive-optics system, and the fundus is imaged.

Figure 1:
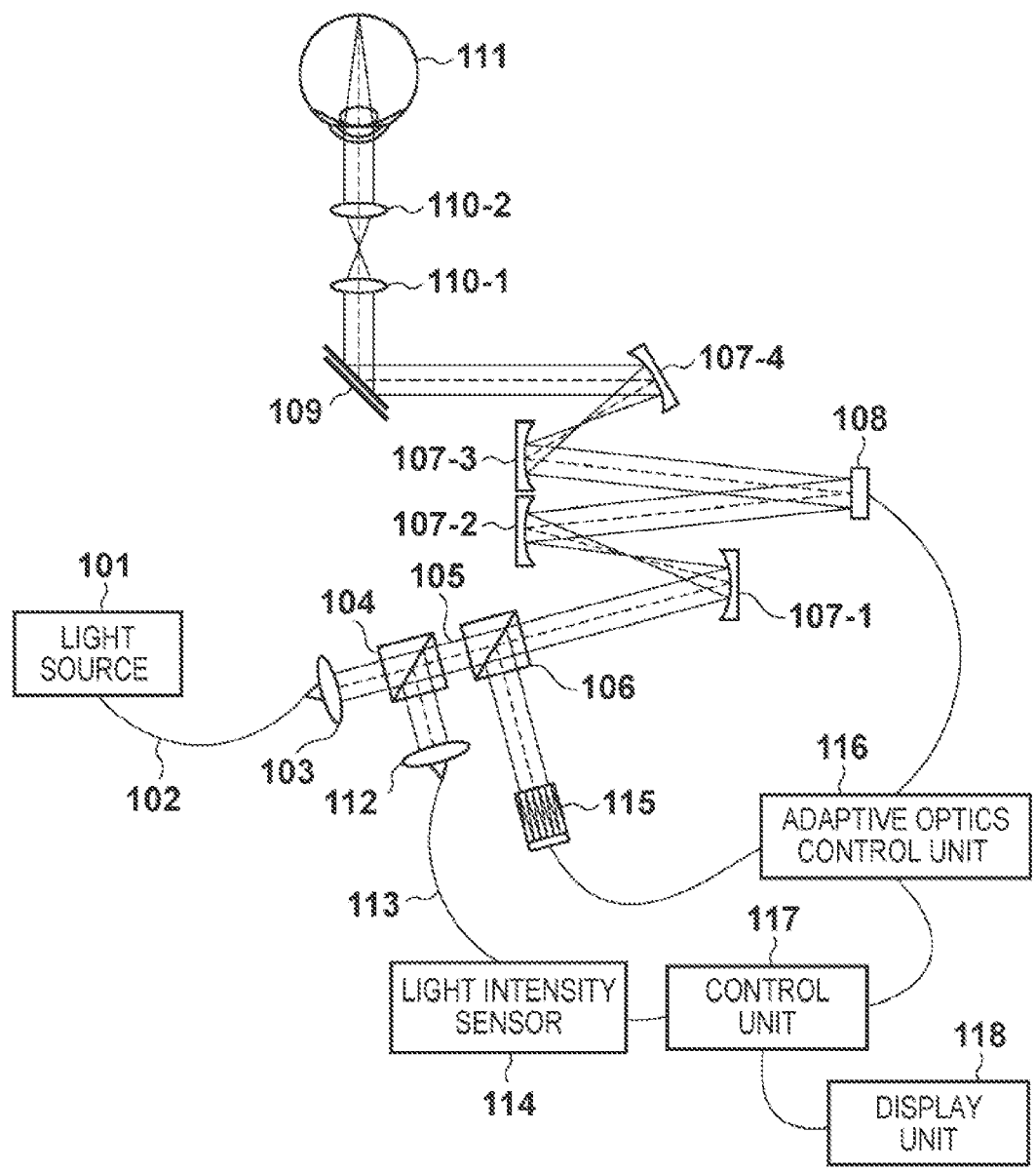
FIG. 1 is a view showing an example of the arrangement of a fundus imaging apparatus based on SLO including an adaptive-optics system according to the first embodiment.

Referring to FIG. 1, this apparatus uses an SLD (Super Luminescent Diode) light source having a wavelength of 840 nm as a light source 101. Although the wavelength of the light source 101 is not specifically limited, a wavelength of about 800 nm to 1,500 nm is used for fundus imaging to reduce the glare of light at an object and maintain resolution. Although this embodiment uses the SLD light source, it is possible to use a laser or the like. Although the embodiment uses the same light source for fundus imaging and wavefront measurement, it is possible to use different light sources to form an arrangement for multiplexing light midway along the optical path.

The light emitted from the light source 101 passes through a single-mode optical fiber 102, and is applied as a parallel light beam (measurement light 105) through a collimator 103. The applied measurement light 105 is transmitted through a light splitting unit 104 formed from a beam splitter, and is guided to an adaptive-optics system. The adaptive-optics system includes a light splitting unit 106, a wavefront sensor 115, a wavefront correction device 108, and reflecting mirrors 107-1 to 107-4 for guiding light to them. This embodiment uses a beam splitter as the light splitting unit 106. The reflecting mirrors 107-1 to 107-4 are arranged to make at least the pupil of an eye 111, the wavefront sensor 115, and the wavefront correction device 108 have an optically conjugated relation.

Figure 2:
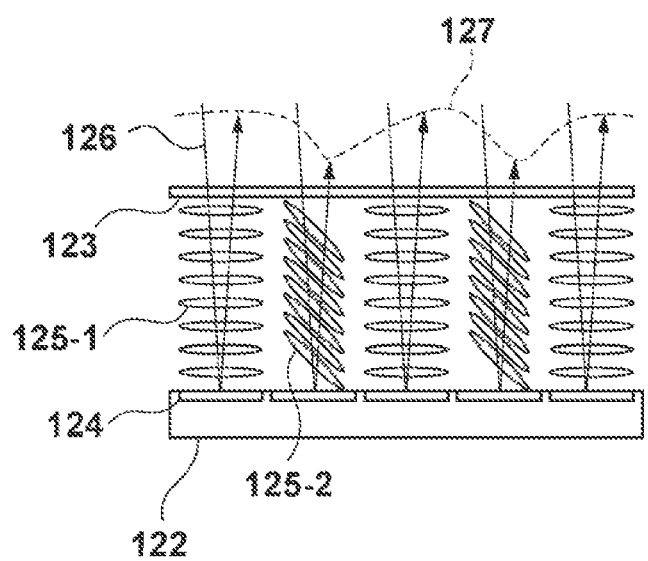
FIG. 2 is a schematic view showing an example of a wavefront correction device in the first embodiment.

The measurement light 105 transmitted through the light splitting unit 106 is reflected by the reflecting mirrors 107-1 and 107-2 and enters the wavefront correction device 108. The measurement light 105 reflected by the wavefront correction device 108 emerges to the reflecting mirror 107-3. This embodiment uses a spatial phase modulator (reflective liquid-crystal optical modulator) using a liquid-crystal device as the wavefront correction device 108. FIG. 2 is a schematic view of a reflective liquid-crystal optical modulator. The reflective liquid-crystal optical modulator has a structure having liquid-crystal molecules sealed in the space defined by a base portion 122 and a cover 123. The base portion 122 has a plurality of pixel electrodes 124, and the cover 123 has a transparent opposite electrode (not shown). In the absence of a voltage between the electrodes, the liquid-crystal molecules exhibit an alignment state like that indicated by "125-1". When a voltage is applied between the electrodes, the liquid-crystal molecules make a transition to an alignment state like that indicated by "125-2", and change in refractive index with respect to incident light. It is possible to perform spatial phase modulation by controlling the voltage to each pixel electrode 124 so as to change its refractive index. When, for example, incident light 126 enters the reflective liquid-crystal optical modulator, light passing through the liquid-crystal molecules 125-2 shows a phase lag relative to light passing through the liquid-crystal molecules 125-1. As a result, a wavefront like that indicated by a broken line 127 in FIG. 2 is formed. In general, the reflective liquid-crystal optical modulator is constituted by several ten thousand to several hundred thousand pixels. In addition, the reflective liquid-crystal optical modulator may include a polarizing unit for adjusting the polarization of incident light so as to have a polarization characteristic.

Figure 3:
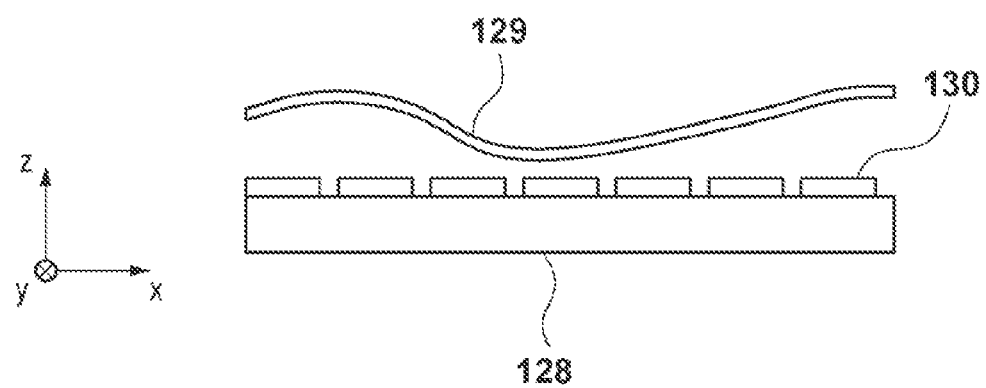
FIG. 3 is a view showing another example of the arrangement of the wavefront correction device.

A deformable mirror is available as another example of the wavefront correction device 108. The deformable mirror can locally change the reflecting direction of light. Various types of deformable mirrors are available. The deformable mirror is formed as, for example, a device having the section shown in FIG. 3, which includes a mirror surface 129 in the form of a deformable film that reflects incident light, a base portion 128, actuators 130 sandwiched between the mirror surface 129 and the base portion 128, and a support portion (not shown) that supports the mirror surface 129 with respect to its surrounding. The principle of operation of the actuators 130 includes using electrostatic force, magnetic force, or the piezoelectric effect. The actuators 130 differ in arrangement depending on the principle of operation. The actuators 130 are two-dimensionally arranged in a plurality of arrays on the base portion 128 within an x-y plane. Selectively driving the actuators 130 can freely deform the mirror surface 129 in the z direction in FIG. 3. In general, a deformable mirror is constituted by several ten to several hundred of actuators.

Referring to FIG. 1, a scanning optical system 109 one-dimensionally or two-dimensionally scans the light reflected by the reflecting mirrors 107-3 and 107-4. In this embodiment, the scanning optical system 109 includes two Galvanometer scanners respectively used for a main scanning operation (the horizontal direction of the fundus) and a sub-scanning operation (the vertical direction of the fundus). For a faster imaging operation, resonant scanners may be used for the main scanning operation of the scanning optical system 109. In order to set the respective scanners in the scanning optical system 109 in an optically conjugated state, the scanning optical system 109 may have an arrangement using optical elements, such as mirrors and lenses, between the respective scanners.

The measurement light 105 scanned by the scanning optical system 109 passes through eyepiece lenses 110-1 and 110-2 and enters the eye 111. The measurement light 105 entering the eye 111 is reflected or scattered by the fundus. Adjusting the positions of the eyepiece lenses 110-1 and 110-2 can optimally irradiate the eye 111 with light in accordance with the diopter of the eye 111. In this case, the eyepiece lenses are used for the eyepiece portion, but it is possible to use spherical mirrors and the like.

The light reflected or scattered by the retina of the eye 111 reversely propagates along the path of the incident light. The light splitting unit 106 then reflects part of the light to the wavefront sensor 115, which in turn uses the light to measure the wavefront of the light beam.

Figure 4A:
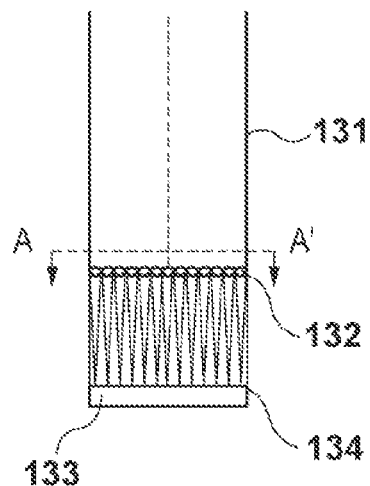
FIGS. 4A and 4B are schematic views showing the arrangement of a Shack-Hartmann wavefront sensor.
Figure 4B:
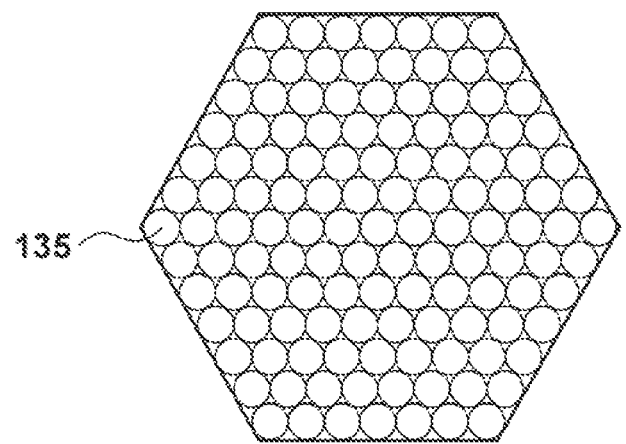
Figure 5:
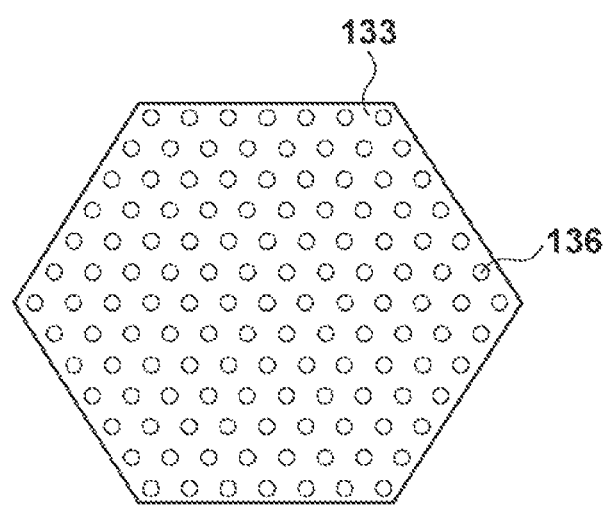
FIG. 5 is a schematic view showing a state in which light beams for measuring a wavefront are focused on a CCD sensor.
Figure 6:
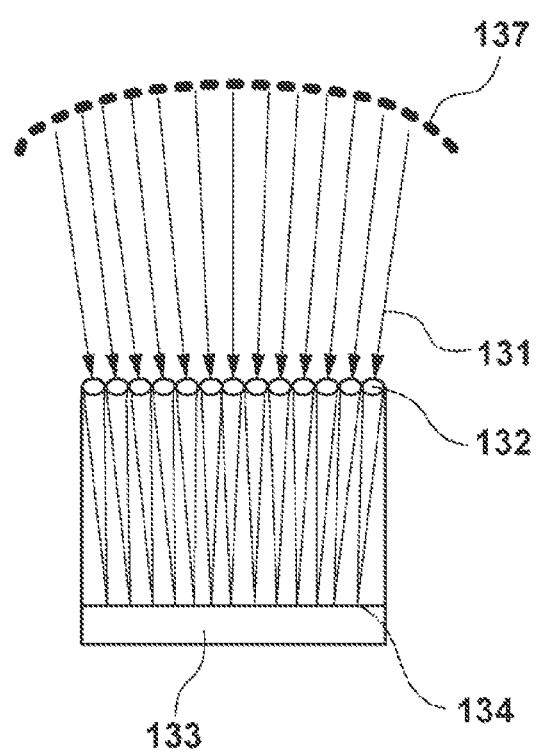
FIG. 6 is a schematic view showing a case in which a wavefront having a spherical aberration is measured.

This embodiment uses a Shack-Hartmann wavefront sensor as the wavefront sensor 115. FIGS. 4A and 4B are schematic views showing the Shack-Hartmann wavefront sensor. Reference numeral 131 denotes a light beam whose wavefront is to be measured, which passes through a microlens array 132 and is focused on a focal plane 134 on a CCD sensor 133. FIG. 4B is a sectional view taken along a line A-A' in FIG. 4A. The microlens array 132 is constituted by a plurality of microlenses 135. The light beam 131 is focused on the CCD sensor 133 through each microlens 135. As a result, the light beam 131 is split into spots corresponding to the number of the microlenses 135 and focused. FIG. 5 shows how light is focused on the CCD sensor 133. The light beam passing through each microlens is focused into a spot 136. The wavefront sensor then calculates the wavefront of the light beams applied from the positions of the spots 136. For example, FIG. 6 is a schematic view showing a case in which a wavefront having a spherical aberration is measured. The light beams 131 are formed by a wavefront like that indicated by a broken line 137. The microlens array 132 focuses the light beams 131 at positions in directions locally perpendicular to the wavefront. FIG. 6 shows a focused state on the CCD sensor 133 in this case. Since the light beam 131 has a spherical aberration, the spot 136 is focused in a state offset to the middle portion. Calculating this position can obtain the wavefront of the light beam 131. This embodiment uses the Shack-Hartmann wavefront sensor for the wavefront sensor 115. However, the gist of the present invention is not limited to this. For example, it is possible to use another type of wavefront measuring unit, such as a curvature sensor or a method of obtaining a wavefront from a formed point image by inverse calculation.

Referring back to FIG. 1, the reflected light transmitted through the light splitting unit 106 in FIG. 1 is partly reflected by the light splitting unit 104 and is guided to a light intensity sensor 114 through a collimator 112 and an optical fiber 113. The light intensity sensor 114 then converts the light into an electrical signal. The CP 117 forms the signal into a fundus image and displays it on a display unit 118.

The wavefront sensor 115 is connected to an adaptive-optics control unit 116 to transfer the received wavefront to the adaptive-optics control unit 116. The wavefront correction device 108 is also connected to the adaptive-optics control unit 116 to perform modulation instructed from the adaptive-optics control unit 116. The adaptive-optics control unit 116 calculates a modulation amount (correction amount) for correction toward a wavefront with no aberration based on the wavefront acquired from the measurement result obtained by the wavefront sensor 115. The adaptive-optics control unit 116 instructs the wavefront correction device 108 to perform modulation based on the modulation amount (correction amount) calculated by the adaptive-optics control unit 116. The adaptive-optics control unit 116 repeatedly instructs the wavefront correction device 108 based on the measurement of a wavefront by the wavefront sensor 115 and the modulation amount (correction amount) calculated based on the measurement result, thus always performing feedback control to obtain an optimal wavefront. In this embodiment, the adaptive-optics control unit 116 models the measured wavefront into a Zernike function and calculates coefficients applied to the respective orders of the function. The adaptive-optics control unit 116 then calculates a modulation amount for the wavefront correction device 108 based on the coefficients. When calculating a modulation amount, the adaptive-optics control unit 116 multiplies the coefficients of all the Zernike orders by reference modulation amounts that allow the wavefront correction device 108 to form the shapes of the respective Zernike orders, and adds up all the products, thereby obtaining a final modulation amount. This embodiment uses a reflective liquid-crystal optical modulator with a pixel count of 600×600 as the wavefront correction device 108, and hence calculates a modulation amount for each of 360,000 pixels in accordance with the above-described calculation method. When, for example, performing a calculation using the coefficients of the first to fourth orders of a Zernike function, the embodiment multiplies 14 coefficients, namely $Z1-1$, $Z1+1$, $Z2-2$, $Z2-0$, $Z2+2$, $Z3-3$, $Z3-1$, $Z3+1$, $Z3+3$, $Z4-4$, $Z4-2$, $Z4-0$, $Z4+2$, and $Z4+4$ by reference modulation amounts for each of the 360,000 pixels. When performing a calculation using the coefficients of the first to sixth orders of the Zernike function, the embodiment multiplies 27 coefficients, namely $Z1-1$, $Z1+1$, $Z2-2$, $Z2-0$, $Z2+2$, $Z3-3$, $Z3-1$, $Z3+1$, $Z3+3$, $Z4-4$, $Z4-2$, $Z4-0$, $Z4+2$, $Z4+4$, $Z5-5$, $Z5-3$, $Z5-1$, $Z5+1$, $Z5+3$, $Z5+5$, $Z6-6$, $Z6-4$, $Z6-2$, $Z6-0$, $Z6+2$, $Z6+4$, and $Z6+6$ by reference modulation amounts for each of the 360,000 pixels. Since the eye to be examined is included in part of the optical system, the state of optical system is uncertain. For this reason, it is generally difficult to reach a wavefront with low aberration by one aberration measurement and correction. Therefore, aberration measurement and correction are repeated to correct the aberration to an extent to allow an imaging operation.

As described above, most of the aberrations of the eye are lower-order aberrations. For this reason, this embodiment performs aberration-correction feedback (first aberration-correction feedback) at high speed by using the coefficients of the lower orders, namely the first to fourth orders, of the Zernike function at the beginning of the start of correction. At a midway stage of aberration correction, the embodiment performs more precise aberration-correction feedback (second aberration-correction feedback) by using the coefficients of the higher orders, namely the first to sixth orders, of the Zernike function. Performing such control makes it possible to perform aberration correction up to a low aberration state at a relatively high speed. This can shorten the time to the start of an imaging operation.

Figure 7:
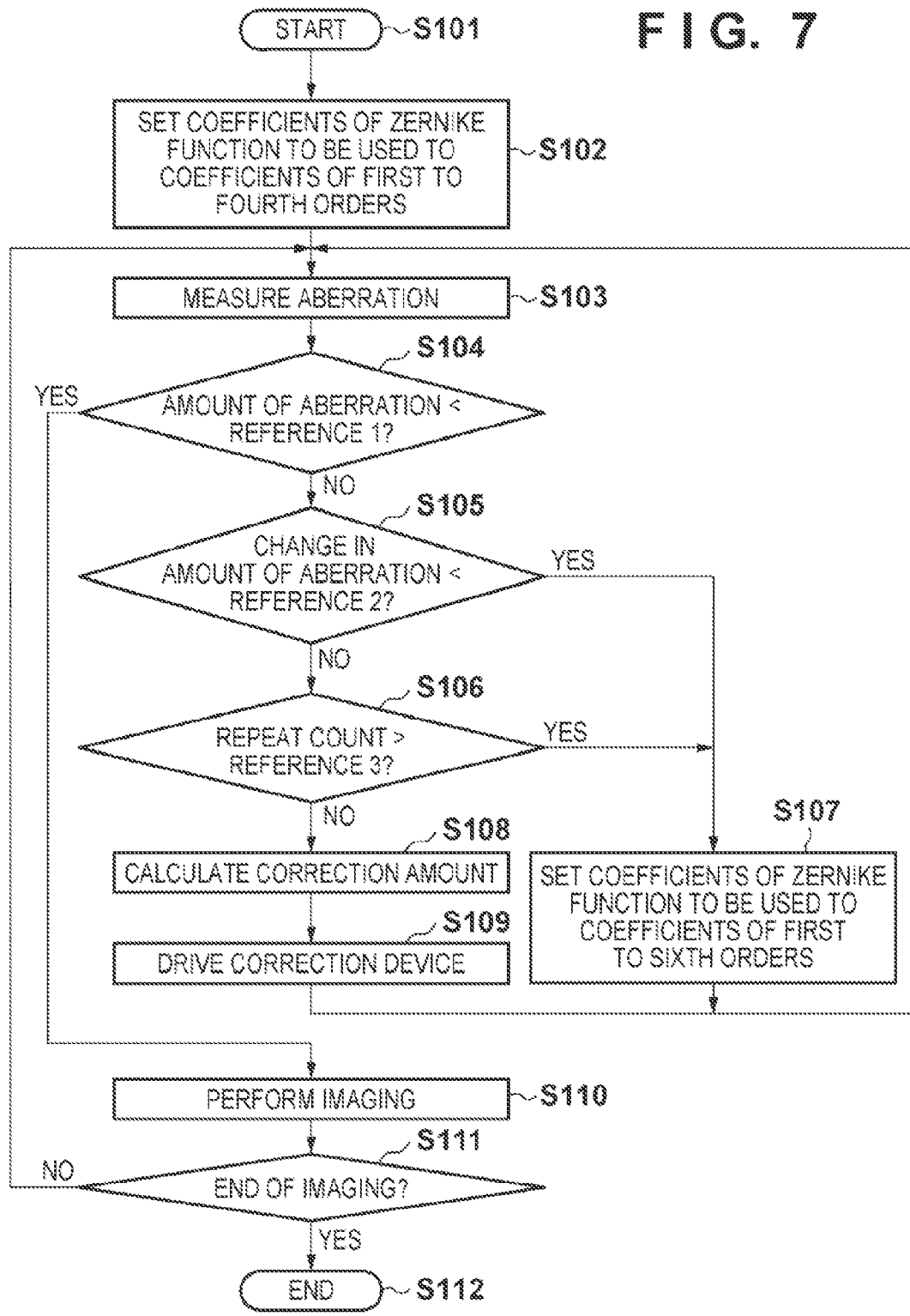
FIG. 7 is a flowchart showing control steps in the fundus imaging apparatus according to the first embodiment.

Processing in the fundus imaging apparatus according to this embodiment will be described with reference to the flowchart of FIG. 7. In step S101, the fundus imaging apparatus starts a control operation. In step S102, the apparatus sets coefficients up to the Nth order (N is a natural number (ditto for the following)) to express an aberration by a Zernike function, which is a polynomial function. In this embodiment, the apparatus sets the coefficients of the Zernike function to be used for aberration correction to the coefficients of the lower orders, namely the first to fourth orders. The apparatus then executes the basic procedure in the adaptive optics from step S103 to step S109 (to be described below). The following is an outline of the basic procedure in the adaptive optics. In step S103, the wavefront sensor 115 measures an aberration. In step S108, the adaptive-optics control unit 116 calculates a correction amount based on the measurement result. In step S109, the apparatus repeatedly drives the wavefront correction device 108 under the control of the adaptive-optics control unit 116.

The contents of each step in the adaptive optics will be described next. In step S103, the wavefront sensor 115 measures an aberration and obtains the amount of aberration. In this embodiment, the amount of aberration indicates the total amount of a wavefront disturbance obtained from the obtained aberration. However, this amount may indicate, for example, the total amount of deviation from a reference wavefront (flat wavefront). In step S104 (first determination step), the adaptive-optics control unit 116 determines whether the amount of aberration obtained in step S103 is smaller than the predetermined first reference value (reference 1). The first reference value (reference 1) may be a value unique to the fundus imaging apparatus or may be set by the operator. If the amount of aberration is smaller than the first reference value (reference 1) (YES in step S104), the process advances to step S110. If the amount of aberration is equal to or more than the first reference value (reference 1) (NO in step S104), the process advances to step S105 to execute the processing in step S105 and the subsequent steps.

In step S105 (second determination step), the adaptive-optics control unit 116 obtains a change in the amount of aberration from the difference between the amount of aberration that has already been measured (for example, the previously measured amount of aberration) and the amount of aberration obtained by the current measurement. The adaptive-optics control unit 116 then determines whether the change in the amount of aberration is smaller than the second reference value (reference 2). It is possible to use, as the second reference value (reference 2), for example, a value representing the rate of change in the difference between the previous amount of aberration and the current amount of aberration or a value determined by the operator in advance. If the change in the amount of aberration is smaller than the second reference value (reference 2) (YES in step S105), the adaptive-optics control unit 116 determines that it is highly possible that the use of the coefficients of the orders currently used may not allow sufficient correction. The process therefore advances to step S107. In step S107, the adaptive-optics control unit 116 changes the Nth-order polynomial function to an Mth-order (M is a natural number satisfying the relation of M>N (ditto for the following)) function including orders higher than the Nth order in accordance with the change between the measured amount of aberration and the amount of aberration measured after correction. The adaptive-optics control unit 116 sets the coefficients of the Zernike function to be used for aberration correction to the coefficients of a function including the higher orders, namely the first to sixth orders. The process then returns to step S103. This embodiment exemplifies the setting of the coefficients of the first to sixth orders as the coefficients of the higher orders. If, however, the coefficients of the first to fourth orders are set as the coefficients of lower orders, the coefficients of higher orders are not limited to the coefficients of the first to sixth orders. For example, it is possible to set the coefficients of the first to fifth orders including the coefficients of the first to fourth orders or the coefficients of the first to sixth orders. In addition, the coefficients of the sixth order are not limited as the upper-limit coefficients, and the coefficients to be used can include those of higher orders.

In step S103 and the subsequent steps, the adaptive-optics control unit 116 performs similar aberration-correction processing by using the function including the coefficients of the higher orders set in step S107 previously executed.

If the adaptive-optics control unit 116 determines in step S105 that the change in the amount of aberration is equal to more than the second reference value (reference 2) (NO in step S105), the unit determines that the aberration correction corresponding to the function including the orders currently used is not sufficient. The adaptive-optics control unit 116 therefore advances the process to step S106 to continue correction without changing the coefficients of the orders currently used.

In step S106 (third determination step), the adaptive-optics control unit 116 determines whether the repeat count of correction control from the start of aberration correction exceeds the third reference value (reference 3). If the repeat count exceeds the third reference value (reference 3) (YES in step S106), the adaptive-optics control unit 116 advances the process to step S107. In step S107, the adaptive-optics control unit 116 changes the function (first function) having predetermined orders to a function (second function) including orders higher than the predetermined orders in accordance with the measurement result obtained by the wavefront sensor 115. In this case, the measurement result obtained by the wavefront sensor 115 includes at least one of the amount of aberration measured by the wavefront sensor 115 and the change in the amount of aberration obtained from the difference between the amount of aberration that has already been measured and the amount of aberration measured by the wavefront sensor 115. The adaptive-optics control unit 116 changes the coefficients of the Zernike function to be used to, for example, the coefficients of a function having orders including the higher orders, namely the first to sixth orders, and returns the process to step S103. Although the above description has exemplified the control result obtained by the adaptive-optics control unit 116 using the repeat count of correction control as the third reference in step S106, the gist of the present invention is not limited to this. For example, it is possible to obtain a control result by using, as the third reference, a repetition time indicating the lapse of time from the start of correction control processing. The adaptive-optics control unit 116 includes a timepiece unit (for example, a timer) capable of measuring the lapse of time from the start of processing, and determines whether a predetermined repetition time has elapsed from the start of correction control processing (S106). After the predetermined repetition time has elapsed from the start of the processing (YES in step S106), the process advances to step S107. In step S107, the adaptive-optics control unit 116 executes the processing of changing the function (first function) having predetermined orders to the function (second function) having orders including orders higher than the predetermined orders in accordance with the measurement result obtained by the wavefront sensor 115.

If the adaptive-optics control unit 116 determines in step S106 that the repeat count of correction control from the start of aberration correction is equal to or smaller than the third reference value (reference 3) (NO in step S106), the process advances to step S108. In step S108, the adaptive-optics control unit 116 calculates a correction amount for the correction of the aberration, which is expressed by the changed function. In step S109, the apparatus drives the wavefront correction device 108 under the control of the adaptive-optics control unit 116, and executes correction processing for the correction of the aberration expressed by the changed function. The process then returns to step S103. The apparatus repeats the processing from step S103 to step S109 until the adaptive-optics control unit 116 determines in step S104 that the amount of aberration is smaller than the first reference value (reference 1).

The fundus imaging apparatus images the fundus of the eye in step S110, and determines in step S111 whether to terminate the processing. If no termination request is input (NO in step S111), the process returns to step S103 to perform the processing in the adaptive optics from step S103 to step S109 and perform imaging in step S110. In the example of the control operation of the fundus imaging apparatus shown in FIG. 7, the apparatus sequentially performs the process for imaging and the process for aberration correction. It is however possible to concurrently perform both the processes. If the apparatus confirms a termination request in step S111 (YES in step S111), the apparatus terminates the control operation in step S112.

In aberration-correction processing, since the calculation time for a modulation amount (correction amount) occupies a very high ratio of the total processing time, a reduction in the calculation amount is very effective in speeding up the processing. The time taken to calculate a modulation amount by using the coefficients of the first to fourth orders of the Zernike function differs from that taken to calculate a modulation amount by using the coefficients of the first to sixth orders of the Zernike function by almost two times. Performing correction by using the coefficients of the first to fourth orders of the Zernike function at the start of correction as in this embodiment will greatly speed up the processing. If most of measured aberrations are aberrations corresponding to the first to fourth orders of the Zernike function, it is possible to sufficiently correct the aberrations by using the coefficients of the first to fourth orders of the Zernike function. The process therefore advances from step S104 to step S110 to allow imaging to quickly start. If sufficient correction could not be performed by using the coefficients of the first to fourth orders of the Zernike function, this apparatus processes only the residual aberrations, which could not be corrected, by using the coefficients of orders including the higher orders of the Zernike function, and hence can reach a ready state for imaging with a small correction count. Performing such processing can correct aberrations that allow imaging faster than repeating control using coefficients including those of the higher orders from the start of processing. This embodiment uses Zernike functions to model aberrations. However, the same applies to a case in which the apparatus uses other function systems.

This embodiment allows the use of a proper correction method in accordance with a correction state, and hence can speed up aberration-correction processing and implement high-speed imaging.

Second Embodiment

Figure 8:
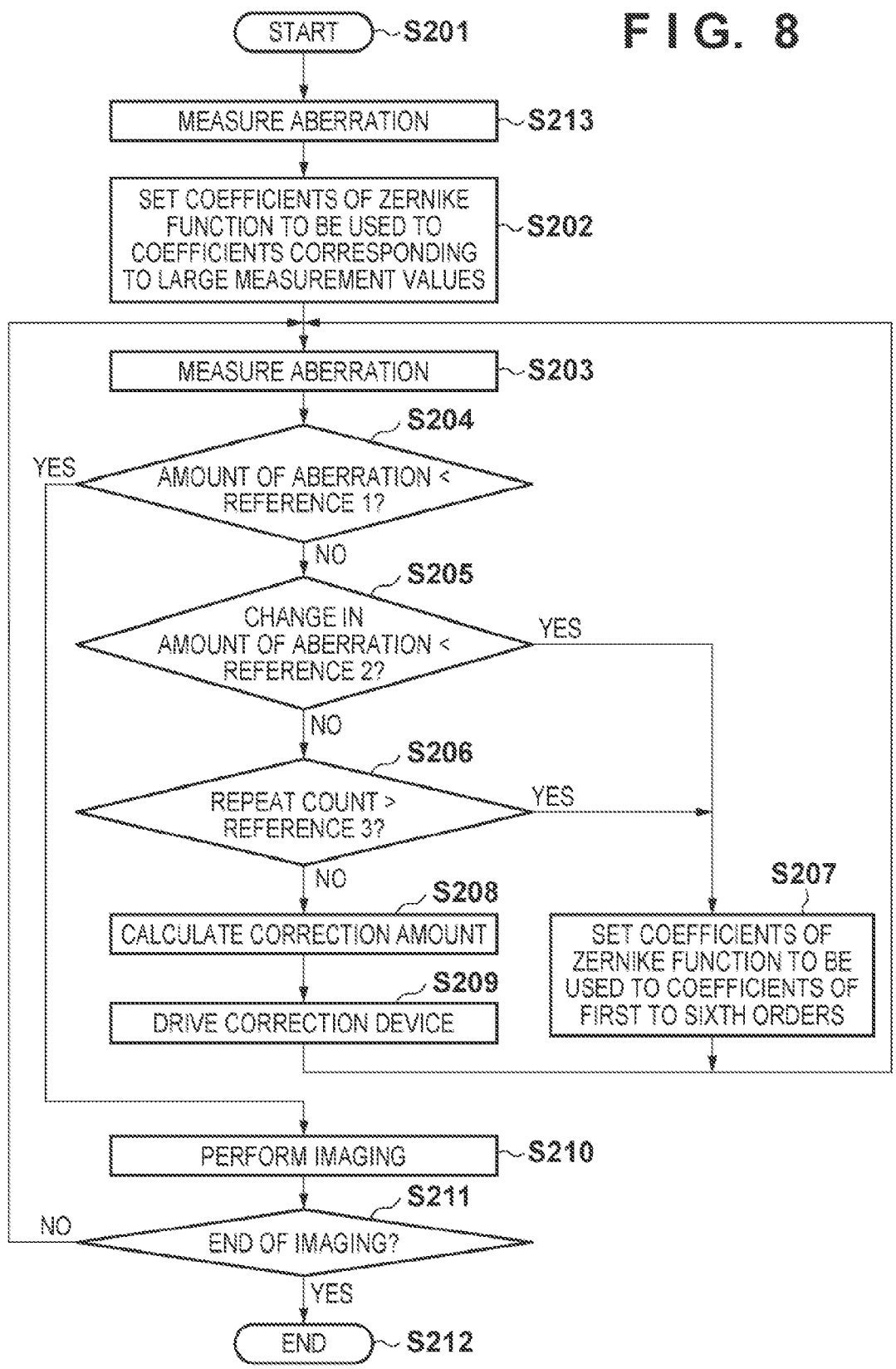
FIG. 8 is a flowchart showing control steps in a fundus imaging apparatus according to the second embodiment.

Processing in a fundus imaging apparatus according to the second embodiment will be described with reference to the flowchart of FIG. 8. The basic apparatus arrangement is the same as that of the first embodiment. This embodiment has a feature of performing aberration correction by using coefficients corresponding to large aberrations of the aberrations of the eye to be examined as dominant coefficients in aberration correction. The fundus imaging apparatus starts a control operation in step S201. In step S213, the apparatus measures an aberration before correction. An adaptive-optics control unit 116 models the measured aberration by using the first to sixth orders of a Zernike function, and checks a term (order) of the modeled terms (orders) which has large coefficients. In step S202, the apparatus sets coefficients for the term (order) having large values checked in step S213 as coefficients to be used for correction control. The apparatus then executes a basic procedure in the adaptive optics.

The following is an outline of the basic procedure in the adaptive optics. In step S203, a wavefront sensor 115 measures an aberration. In step S208, the adaptive-optics control unit 116 calculates a correction amount based on the measurement result. In step S209, the apparatus repeatedly drives a wavefront correction device 108 under the control of the adaptive-optics control unit 116. The contents of each step in the adaptive optics will be described next. In step S203, the wavefront sensor 115 measures an aberration and obtains an amount of aberration.

In step S204, the adaptive-optics control unit 116 determines whether the amount of aberration obtained in step S203 is smaller than the predetermined first reference value (reference 1). The first reference value (reference 1) may be a value unique to the fundus imaging apparatus or may be set by the operator. If the amount of aberration is smaller than the first reference value (reference 1) (YES in step S204), the process advances to step S110. If the amount of aberration is equal to or more than the first reference value (reference 1) (NO in step S204), the process advances to step S205 to execute the processing in step S205 and the subsequent steps.

In step S205, the adaptive-optics control unit 116 then determines whether a change in the amount of aberration exceeds the second reference value (reference 2). If the change in the amount of aberration is smaller than the second reference value (reference 2) (YES in step S205), the adaptive-optics control unit 116 determines that it is highly possible that the use of the coefficient of the orders currently used may not allow sufficient correction. The process therefore advances to step S207. In step S207, the adaptive-optics control unit 116 changes the coefficients of the Zernike function to be used to the coefficients of a function having higher orders, namely the first to sixth orders (a function having the correction coefficients of higher orders), and returns the process to step S203. In step S203 and the subsequent steps, the adaptive-optics control unit 116 performs similar aberration-correction processing by using the function having the higher orders changed in step S207.

If the adaptive-optics control unit 116 determines in step S205 that the change in the amount of aberration is equal to or more than the second reference value (reference 2) (NO in step S205), the unit determines that the aberration correction corresponding to the coefficients of the function currently used is not sufficient. The adaptive-optics control unit 116 therefore advances the process to step S206 to continue correction without changing the coefficients of the orders currently used.

In step S206, the adaptive-optics control unit 116 determines whether the repeat count of correction control from the start of aberration correction exceeds the third reference value (reference 3). In this case, the third reference value (reference 3) is a predetermined constant N (N is a natural number equal to or more than 2). If the repeat count exceeds the third reference value (reference 3) (YES in step S206), the adaptive-optics control unit 116 advances the process to step S207. In step S207, the adaptive-optics control unit 116 changes the coefficients of the Zernike function to be used to the coefficients of orders including the higher orders, namely the first to sixth orders, (correction coefficients of the higher orders), and returns the process to step S203.

If the adaptive-optics control unit 116 determines in step S206 that the repeat count of correction control from the start of aberration correction is equal to or smaller than the third reference value (reference 3) (NO in step S206), the process advances to step S208. In step S208, the adaptive-optics control unit 116 calculates a correction amount. In step S209, the apparatus drives the wavefront correction device 108 under the control of the adaptive-optics control unit 116. The process then returns to step S203. The apparatus repeats the processing from step S203 to step S209 until the adaptive-optics control unit 116 determines in step S204 that the amount of aberration is smaller than the first reference value (reference 1).

The fundus imaging apparatus images the fundus of the eye in step S210, and determines in step S211 whether to terminate the processing. If no termination request is input (NO in step S211), the process returns to step S203 to perform the processing in the adaptive optics from step S203 to step S209 and perform imaging in step S210. In the example of the control operation of the fundus imaging apparatus shown in FIG. 8, the apparatus sequentially performs the process for imaging and the process for aberration correction. It is however possible to concurrently perform both the processes. If the apparatus confirms a termination request in step S211 (YES in step S211), the apparatus terminates the control operation in step S212.

Limiting orders to be corrected at the start of correction to portions having large aberrations can greatly speed up the processing. Since orders having large aberrations are correction targets, it is highly possible to reach an aberration state allowing imaging by correcting these orders. This makes it possible to quickly start imaging. Even if the aberrations cannot be corrected with the initial settings, since the apparatus corrects only the residual aberrations which could not be corrected, it is therefore possible to reach an aberration state allowing imaging more quickly than repeating control using the coefficients of orders including higher orders from the beginning of the processing. This embodiment uses Zernike functions to model aberrations. The same applied to a case in which the apparatus uses other function systems.

This embodiment allows to use a proper correction method in accordance with the aberration state of the eye to be examined, and hence can speed up aberration-correction processing and implement high-speed imaging.

Third Embodiment

Figure 9:
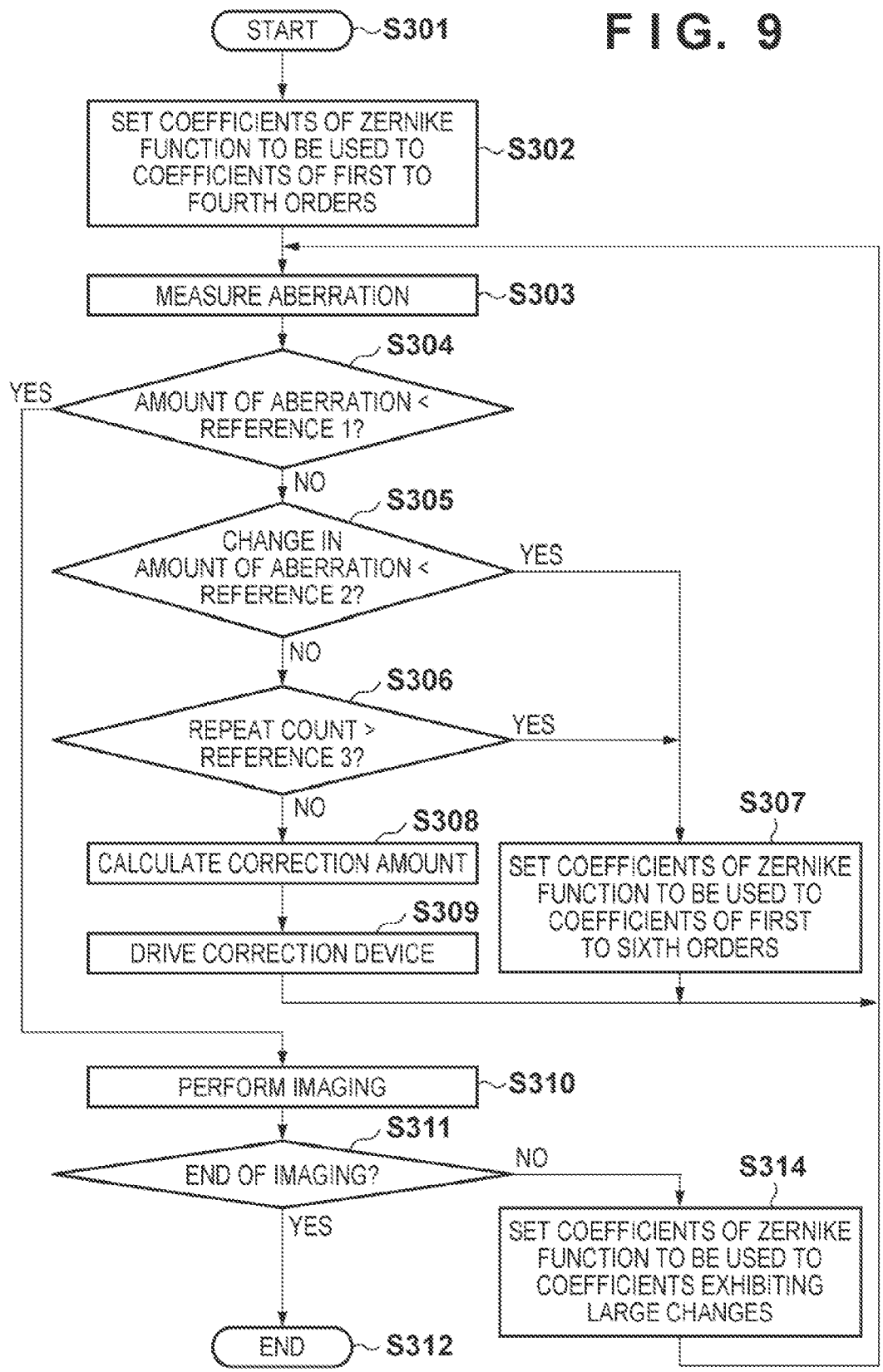
FIG. 9 is a flowchart showing control steps in a fundus imaging apparatus according to the third embodiment.

Processing in a fundus imaging apparatus according to the third embodiment will be described with reference to the flowchart of FIG. 9. The basic apparatus arrangement is the same as that of the first embodiment. This embodiment has a feature of speeding up correction control to improve maintenance accuracy in an arrangement for maintaining a low aberration state after the completion of correction up to aberrations allowing fundus imaging.

In step S301, the fundus imaging apparatus starts a control operation. In step S302, the apparatus sets coefficients up to the Nth order to express an aberration by a Zernike function, which is a polynomial function. In this embodiment, the apparatus sets the coefficients of the Zernike function to be used for aberration correction to the coefficients of the lower orders, namely the first to fourth orders. The apparatus then executes the basic procedure in the adaptive optics from step S303 to step S309 (to be described below). The following is an outline of the basic procedure in the adaptive optics. In step S303, a wavefront sensor 115 measures an aberration. In step S308, an adaptive-optics control unit 116 calculates a correction amount based on the measurement result. In step S309, the apparatus repeatedly drives a wavefront correction device 108 under the control of the adaptive-optics control unit 116.

The contents of each step in the adaptive optics will be described next. In step S303, the wavefront sensor 115 measures an aberration and obtains the amount of aberration.

In step S304, the adaptive-optics control unit 116 determines whether the amount of aberration obtained in step S303 is smaller than the predetermined first reference value (reference 1). The first reference value (reference 1) may be a value unique to the fundus imaging apparatus or may be set by the operator. If the amount of aberration is smaller than the first reference value (reference 1) (YES in step S304), the process advances to step S310. If the amount of aberration is equal to or more than the first reference value (reference 1) (NO in step S304), the process advances to step S305 to execute the processing in step S305 and the subsequent steps. As in the processing in steps S105 and S106 in the first embodiment, the adaptive-optics control unit 116 determines the rate of change in the amount of aberration and the repeat count in steps S305 and S306. The adaptive-optics control unit 116 then compares each value with a corresponding reference value. If they coincide with each other (YES in step S305 and YES in step S306), the process advances to step S307. In step S307, the adaptive-optics control unit 116 changes the Nth-order (N is a natural number) function to an Mth-order (M is a natural number satisfying the relation of M>N) function including orders higher than the Nth order in accordance with the change between the measured amount of aberration and the amount of aberration measured after correction. The adaptive-optics control unit 116 sets the coefficients of the Zernike function to be used to the coefficients of a function including the higher orders, namely the first to sixth orders. The process then returns to step S103. This embodiment exemplifies the setting of the coefficients of the first to sixth orders as the coefficients of the higher orders. If, however, the coefficients of the first to fourth orders are set as the coefficients of lower orders, the coefficients of higher orders are not limited to the coefficients of the first to sixth orders. For example, it is possible to set the coefficients of the first to fifth orders including the coefficients of the first to fourth orders or the coefficients of the first to sixth orders. In addition, the coefficient of the sixth order are not limited as the upper-limit coefficients, and the coefficients to be used can include those of higher orders.

If the adaptive-optics control unit 116 determines upon comparison with the respective reference values in steps S305 and S306 that the respective values do not coincide with the set conditions (NO in step S305 and NO in step S306), the process advances to step S308. In step S308, the adaptive-optics control unit 116 calculates a correction amount. In step S309, the apparatus drives the wavefront correction device 108 under the control of the adaptive-optics control unit 116. The process then returns to step S303. The apparatus repeats the processing from step S303 to step S309 until the adaptive-optics control unit 116 determines in step S304 that the amount of aberration is smaller than the first reference value (reference 1).

The fundus imaging apparatus images the fundus of the eye in step S310, and determines in step S311 whether to terminate the processing. If the apparatus confirms a termination request in step S311 (YES in step S311), the apparatus terminates the control operation in step S312.

If the adaptive-optics control unit 116 determines in step S311 that no termination request has been input (NO in step S311), the process advances to step S314. In step S314, the adaptive-optics control unit 116 selects the coefficients of an order exhibiting a large change (fluctuation) from the measured aberration, and sets the coefficients of the order as coefficients to be used for correction. It is possible to select, as coefficients to be used for correction, any number of coefficients exhibiting large fluctuation amounts or the coefficients of orders corresponding to a predetermined fluctuation amount or more. In measuring, for example, the undilated eye, since the refraction adjustment of the eye always fluctuates, it is necessary to follow up this refracted state in order to perform imaging with high image quality. In this case, since lower-order aberrations greatly fluctuate, performing aberration correction by using the coefficients of lower orders improves the follow-up performance. It is known that higher-order aberrations fluctuate depending on the state of tear fluid. If, therefore, higher-order aberrations greatly fluctuate, aberration correction may be performed by using the coefficients of higher orders.

After setting coefficients, the apparatus performs basic processing of the adaptive optics in step S303 and the subsequent steps, and then performs the next imaging operation in step S310. In the example of the control operation of the fundus imaging apparatus shown in FIG. 9, the apparatus sequentially performs the process for imaging and the process for aberration correction. It is however possible to concurrently perform both the processes.

This embodiment improves the follow-up performance for aberration correction at the time of continuous imaging operation, and hence can capture a plurality of high-quality images in a short period of time.

Fourth Embodiment

Figure 10:
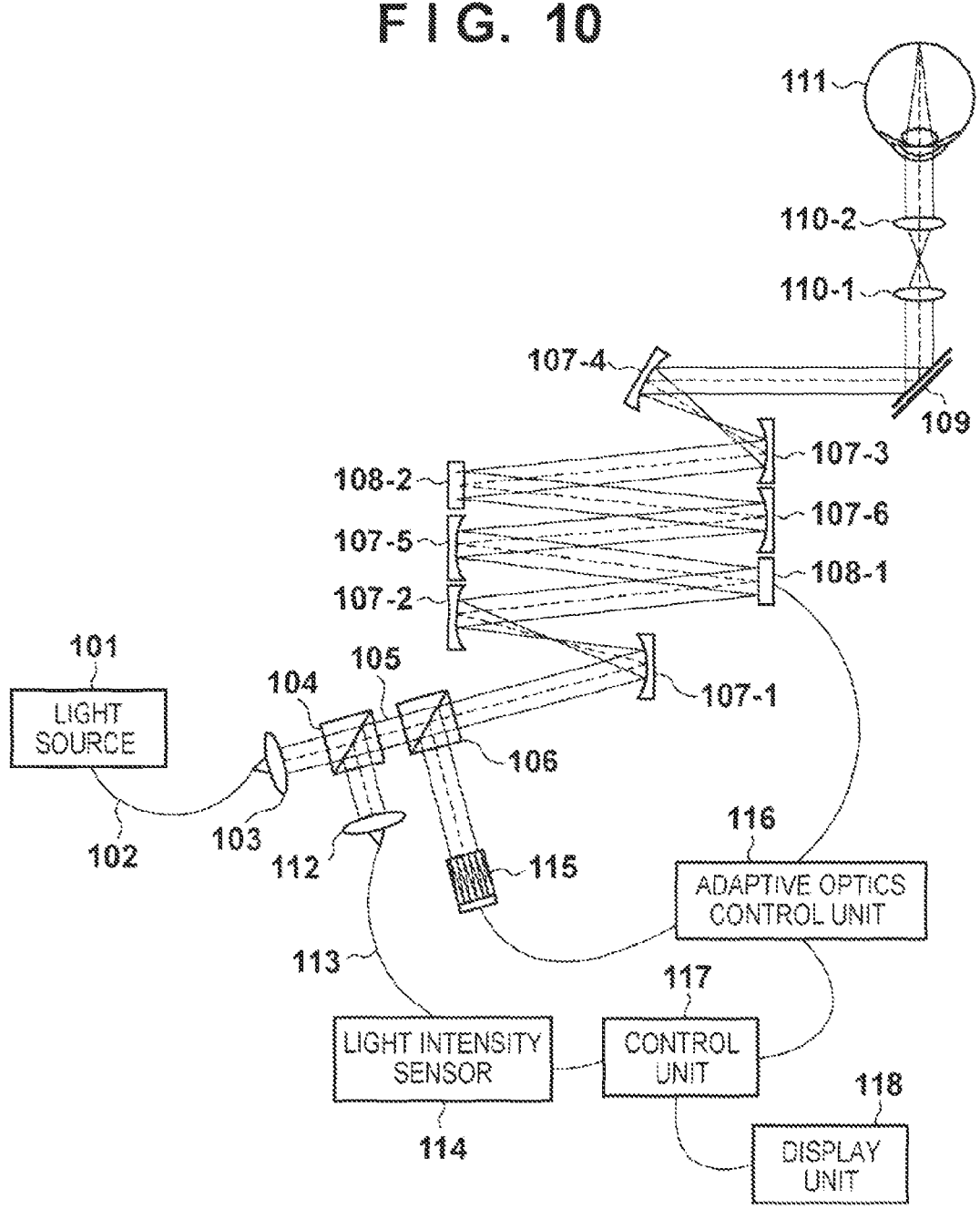
FIG. 10 is a view showing an example of the arrangement of a fundus imaging apparatus based on SLO including an adaptive-optics system according to the fourth embodiment.

The arrangement of a fundus imaging apparatus according to the fourth embodiment will be described with reference to FIG. 10. The basic arrangement shown in FIG. 10 is the same as that of the fundus imaging apparatus of the first embodiment, and the same reference numerals denote the same constituent elements. In the fundus imaging apparatus according to the fourth embodiment, a wavefront correction device 108 is constituted by a first wavefront correction device 108-1 and a second wavefront correction device 108-2. The fundus imaging apparatus includes reflecting mirrors 107-5 and 107-6 for optically coupling the first wavefront correction device 108-1 to the second wavefront correction device 108-2. In this case, the first wavefront correction device 108-1 is designed to mainly correct lower-order aberrations. For example, a deformable mirror including a small number of elements is suitably used as this device. The second wavefront correction device 108-2 is designed to correct aberrations including higher-order aberrations. A deformable mirror including a large number of elements or a spatial phase modulator (reflective liquid-crystal optical modulator) using a liquid-crystal device is suitably used as this device. An adaptive-optics control unit 116 repeatedly controls processing performed by a wavefront sensor 115 and the first wavefront correction device 108-1 or processing performed by the wavefront sensor 115 and the first and second wavefront correction devices 108-1 and 108-2.

Figure 11:
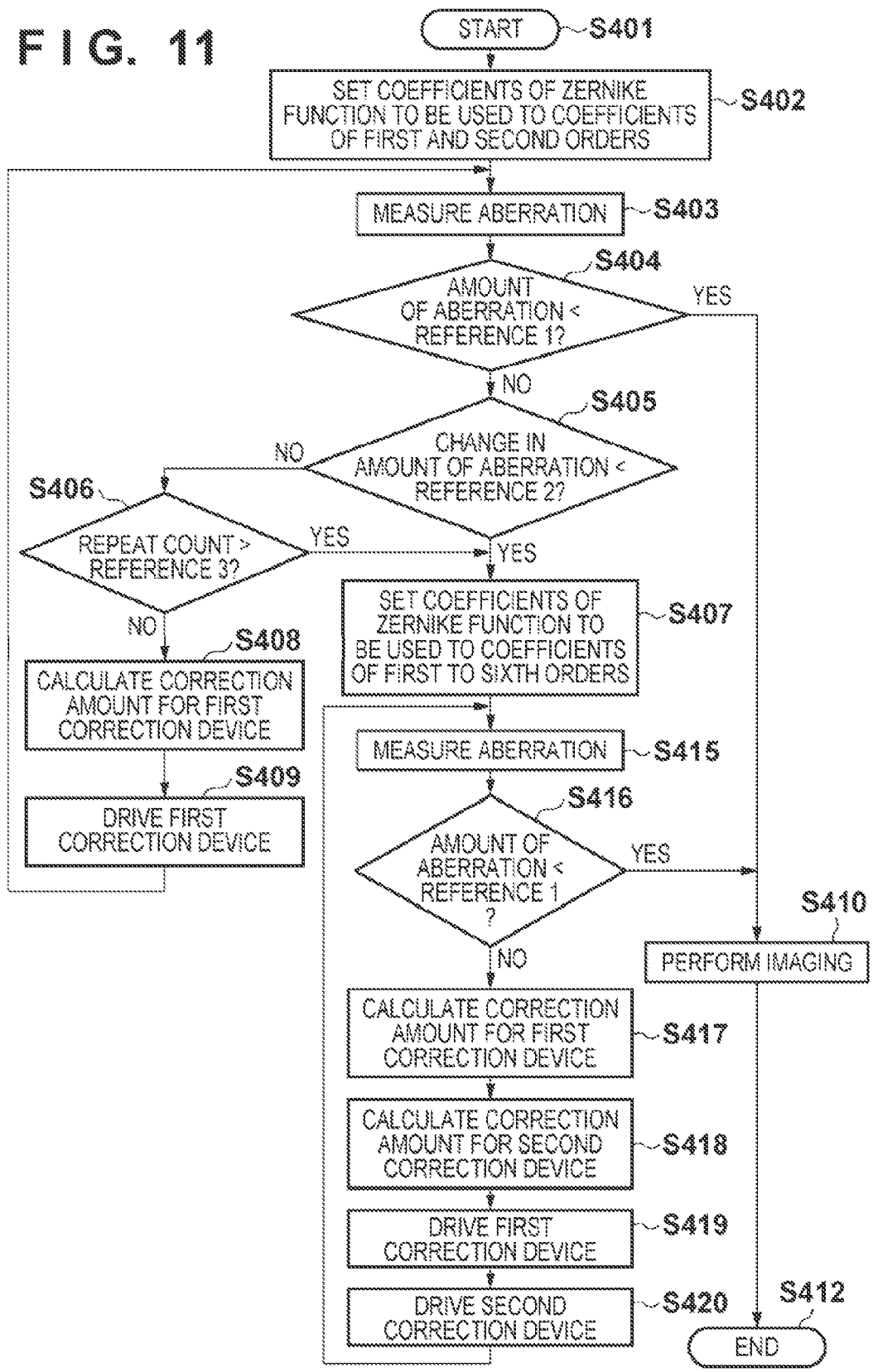
FIG. 11 is a flowchart showing control steps in the fundus imaging apparatus according to the fourth embodiment.

Processing in the fundus imaging apparatus according to the fourth embodiment will be described with reference to the flowchart of FIG. 11. In step S401, the fundus imaging apparatus starts a control operation. In step S402, the apparatus sets coefficients up to the Nth order (N is a natural number) to express an aberration by a Zernike function, which is a polynomial function. In this embodiment, the apparatus sets the Zernike coefficients to be used for aberration correction to the coefficients of the first and second orders. The apparatus then executes the basic procedure in the adaptive optics in steps S403 to S409 (to be described below). The following is an outline of the basic procedure in the adaptive optics. In step S403, the wavefront sensor 115 measures an aberration. In step S408 (first calculation step), the adaptive-optics control unit 116 calculates a correction amount for the first wavefront correction device 108-1 based on the measurement result. Note that in step S408, the adaptive-optics control unit 116 calculates no correction amount for the second wavefront correction device 108-2. Limiting the target for the calculation of a correction amount to the first wavefront correction device 108-1 can reduce the calculation amount and greatly speed up the processing. In step S409, the apparatus repeatedly drives the first wavefront correction device 108-1 under the control of the adaptive-optics control unit 116.

The contents of each step in the adaptive optics will be described next. In step S403, the wavefront sensor 115 measures an aberration and obtains the amount of aberration. In step S404, the adaptive-optics control unit 116 determines whether the amount of aberration obtained in step S403 is smaller than the predetermined first reference value (reference 1). The first reference value (reference 1) may be a value unique to the fundus imaging apparatus or may be set by the operator. If the amount of aberration is smaller than the first reference value (reference 1) (YES in step S404), the process advances to step S410. If the amount of aberration is equal to or more than the first reference value (reference 1) (NO in step S404), the process advances to step S405 to execute the processing in step S405 and the subsequent steps.

As in the processing in steps S105 and S106 in the first embodiment, the adaptive-optics control unit 116 determines the rate of change in the amount of aberration and the repeat count in steps S405 and S406. The adaptive-optics control unit 116 then compares each value with a corresponding reference value. If they coincide with each other (YES in step S405 and YES in step S406), the process advances to step S407. In step S407, the adaptive-optics control unit 116 changes the Nth-order (N is a natural number) function to an Mth-order (M is a natural number satisfying the relation of M>N) function including orders higher than the Nth order in accordance with the change between the measured amount of aberration and the amount of aberration measured after correction. The adaptive-optics control unit 116 sets the coefficients of the Zernike function to be used to the coefficients of a function including the higher orders, namely the first to sixth orders. This embodiment exemplifies the setting of the coefficients of the first to sixth orders as the coefficients of the higher orders. If, however, the coefficients of the first and second orders are set as the coefficients of lower orders, the coefficients of higher orders are not limited to the coefficients of the first to sixth orders. For example, it is possible to set the coefficients of the first to third orders including the coefficients of the first and second orders, the coefficients of the first to fourth orders, and the coefficients of the first to fifth orders or the first to sixth orders. In addition, the coefficient of the sixth order are not limited as the upper-limit coefficients, and the coefficients to be used can include those of higher orders. The Mth order as a higher order need not always include all the coefficients of the Nth order as a lower order. If, for example, the coefficients of the first and second orders are set as the coefficients of the Nth order, it is possible to define the coefficients of a function representing an aberration by setting coefficients so as to include the coefficients of the second order as some of the coefficients of the Nth order and the coefficients of orders higher than the Nth order (for example, the third and fourth orders).

If the adaptive-optics control unit 116 determines upon comparison with the respective reference values in steps S405 and S406 that the respective values do not coincide with the set conditions (NO in step S405 and NO in step S406), the adaptive-optics control unit 116 determines not to change the function (first function) represented by a polynomial having predetermined orders (for example, N orders).

The process advances to step S408. In step S408 (third calculation step), the adaptive-optics control unit 116 calculates a correction amount for the first wavefront correction device 108-1. In step S409 (third aberration correction step), the apparatus drives the first wavefront correction device 108-1 under the control of the adaptive-optics control unit 116 to correct an aberration of predetermined orders (for example, N orders) based on the correction amount calculated in step S408. The process then returns to step S403. The apparatus repeats the processing from step S403 to step S409 until the adaptive-optics control unit 116 determines in step S404 that the amount of aberration is smaller than the first reference value (reference 1).

The fundus imaging apparatus images the fundus of the eye in step S410, and terminates the processing in step S411. As in step S111 in the first embodiment, the apparatus can check the termination of imaging before step S412, and perform continuous imaging.

In step S407, upon changing the Zernike coefficients, the apparatus changes the function to be used to a function (second function) including orders (for example, M orders (M is a natural number satisfying the relation of M>N)) higher than the predetermined orders (for example, N orders) of the function (first function). The process then advances to step S415. Although the processing from step S415 to step S420 is the same as that in the basic procedure in the adaptive optics described above, they differ in that both the first wavefront correction device 108-1 and the second wavefront correction device 108-2 are targets for wavefront correction.

In step S415, the wavefront sensor 115 measures an aberration and obtains the amount of aberration. In step S416, the adaptive-optics control unit 116 determines whether the amount of aberration obtained in step S415 is smaller than the predetermined first reference value (reference 1). If the amount of aberration is smaller than the first reference value (reference 1) (YES in step S416), the process advances to step S410. Upon imaging the fundus in step S410, the apparatus terminates the processing in step S412.

If the apparatus determines in step S416 that the amount of aberration is equal to or more than the first reference value (reference 1) (NO in step S416), the process advances to step S417 to execute the processing in step S417 and the subsequent steps. In step S417, the apparatus expresses the measured aberration by a function having coefficients of orders higher than predetermined orders. The adaptive-optics control unit 116 then calculates a correction amount with which the first wavefront correction device 108-1 (first aberration correction unit) performs aberration correction of a predetermined order for the aberration expressed by the function. Since the first wavefront correction device 108-1 corrects only a lower-order aberration, the adaptive-optics control unit 116 calculates, in step S417, only a correction amount for the lower-order aberration of the aberrations measured in step S415.

In step S418 (second calculation step), the apparatus expresses the measured aberration by a function having coefficients of orders higher than predetermined orders. The adaptive-optics control unit 116 calculates a correction amount with which the second wavefront correction device 108-2 (second aberration correction unit) performs aberration correction of the orders higher than the predetermined orders for the aberration expressed by the function. Since the second wavefront correction device 108-2 corrects only a higher-order aberration, the adaptive-optics control unit 116 calculates, in step S418, only a correction amount for the higher-order aberration of the aberrations measured in step S415.

In step S419 (first aberration correction step), the apparatus drives the first wavefront correction device 108-1 under the control of the adaptive-optics control unit 116 to correct an aberration of predetermined orders of the aberrations expressed by the function including the coefficients of the changed higher orders. In step S420 (second aberration correction step), the apparatus drives the second wavefront correction device 108-2 to correct an aberration, of the aberrations expressed by the function including the coefficients of the changed higher orders, which has an order higher than the predetermined order.

In the processing in step S415 and the subsequent steps, the apparatus is configured to simultaneously control the two wavefront correction devices. However, the apparatus can be configured to perform aberration correction by using only the second wavefront correction device in step S415 and the subsequent steps. In this case, the second wavefront correction device corrects aberrations including lower- and higher-order aberrations that could not be sufficiently corrected by the first wavefront correction device in steps S408 and S409.

According to this embodiment, it is possible to efficiently control a plurality of wavefront correction devices and quickly capture high-quality images.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-283728, filed Dec. 20, 2010, which is hereby incorporated by reference herein in its entirety.

What is claimed is:

1. A fundus imaging method for a fundus imaging apparatus including (a) an aberration measurement unit configured to measure an aberration of reflected light obtained by irradiating an object to be examined with measurement light, (b) an aberration correction unit configured to correct the aberration of light in accordance with the measured aberration, and (c) a control unit configured to repeatedly control processing of the aberration measurement unit and the aberration correction unit, the method comprising:

a selecting step of selecting between a first function including a predetermined order representing the aberration and a second function including an order higher than the predetermined order in accordance with at least one of a measurement result obtained by the aberration measurement unit and a control result obtained by the control unit, wherein the first function includes coefficients of Nth-order to Mth-order representing the aberration (N and M are natural numbers satisfying a relation of M>N), and the second function includes coefficients of Nth-order to Lth-order representing the aberration (L is a natural number satisfying a relation of M<L, M≠L); and an aberration correction step of correcting an aberration expressed by the first function or the second function based on a result of the selecting step.

2. The method according to claim 1, wherein the measurement result obtained by the aberration measurement unit includes at least one of the measured amount of aberration and a change in an amount of aberration obtained from a difference between an amount of aberration which has already been measured and the measured amount of aberration, and
wherein the control result obtained by the control unit is one of a repeat count of the number of times of processing control by the control unit and a repetition time indicating a lapse of time from a start of the processing.

3. The method according to claim 1, further comprising:
a first determination step of determining whether the amount of aberration of the reflected light measured by the aberration measurement unit is less than a first reference value, and
a second determination step of determining whether the change in the amount of aberration is less than a second reference value, when the amount of aberration is not less than the first reference value,
wherein if it is determined that the change in the amount of aberration is less than the second reference value, the second function is selected in the selecting step.

4. The method according to claim 3, further comprising a third determination step of determining whether the repeat count of the number of times of processing by the aberration correction unit exceeds a third reference value, when the change in the amount of aberration is not less than the second reference value,
wherein if it is determined that the repeat count of the number of times of processing by the aberration correction unit exceeds the third reference value, the second function is selected in the selecting step.

5. The method according to claim 1, wherein after the processing controlled by the control unit is repeated by a predetermined repeat count or a predetermined repetition time has elapsed from the start of the processing, the second function is selected in accordance with the measurement result obtained by the aberration measurement unit in the selecting step.

6. The method according to claim 1, further comprising a calculation step of calculating a correction amount for correction of the aberration expressed by the function selected in the selecting step.

7. The method according to claim 1, wherein the aberration correction unit includes a first aberration correction unit and a second aberration correction unit, and the control unit repeatedly controls one of processing by the aberration measurement unit and the first aberration correction unit and processing of the aberration measurement unit, the first aberration correction unit, and the second aberration correction unit, and
wherein the aberration correction step includes
(a) a first aberration correction step of causing the first aberration correction unit to correct an aberration, of aberrations expressed by the second function selected in the selecting step, which has the predetermined order, if the second function is selected in the selecting step,
(b) a second aberration correction step of causing the second aberration correction unit to correct an aberration, of aberrations expressed by the second function selected in the selecting step, which has an order higher than the predetermined order, and
(c) a third aberration correction step of causing the first aberration correction unit configured to correct an aberration of the predetermined order to correct an aberration expressed by the first function including the predetermined order.

8. The method according to claim 7, wherein the first aberration correction step includes a first calculation step of calculating a correction amount with which the first aberration correction unit corrects an aberration expressed by the second function selected in the selecting step,
wherein the second aberration correction step includes a second calculation step of calculating a correction amount with which the second aberration correction unit corrects an aberration expressed by the second function selected in the selecting step, and
wherein the third aberration correction step includes a third calculation step of calculating a correction amount with which the first aberration correction unit corrects an aberration expressed by the first function including the predetermined order.

9. The method according to claim 1, wherein the function is a Zernike function.

10. A fundus imaging apparatus comprising:
an aberration measurement unit configured to measure an aberration of reflected light obtained by irradiating an object to be examined with measurement light;
an aberration correction unit configured to correct an aberration of light in accordance with the measured aberration;
a control unit configured to repeatedly control processing of said aberration measurement unit and said aberration correction unit; and
a selecting unit configured to select between a first function including a predetermined order representing the aberration and a second function including an order higher than the predetermined order in accordance with at least one of a measurement result obtained by said aberration measurement unit and a control result obtained by said control unit,
wherein the first function includes coefficients of Nth-order to Mth-order representing the aberration (N and M are natural numbers satisfying a relation of M>N), and the second function includes coefficients of Nth-order to Lth-order representing the aberration (L is a natural number satisfying a relation of M<L, M≠L), and
wherein said aberration correction unit corrects an aberration expressed by the first function or the second function.

11. The apparatus according to claim 10, wherein the measurement result obtained by said aberration measurement unit includes at least one of the measured amount of aberration and a change in an amount of aberration obtained from a difference between an amount of aberration which has already been measured and the measured amount of aberration, and
wherein the control result obtained by said control unit is one of a repeat count of the number of times said control unit performs processing control and a repetition time indicating a lapse of time from a start of the processing.

12. The apparatus according to claim 10, further comprising:
a first determination unit configured to determine whether an amount of aberration of the reflected light measured by said aberration measurement unit is less than a first reference value, and
a second determination unit configured to determine whether the change in the amount of aberration is less than a second reference value, when the amount of aberration is not less than the first reference value,
wherein if it is determined that the change in the amount of aberration is less than the second reference value, said selecting unit selects the second function.

13. The apparatus according to claim 10, further comprising a third determination unit configured to determine whether the repeat count of the number of times of the processing by said aberration correction unit exceeds a third reference value, when the change in the amount of aberration is not less than the second reference value,
wherein if it is determined that the repeat count of the processing exceeds the third reference value, said selecting unit selects the second function.

14. The apparatus according to claim 10, wherein after the processing controlled by the control unit is repeated by a predetermined repeat count or a predetermined repetition time has elapsed from the start of the processing controlled by the control unit, said selecting unit selects the second function in accordance with the measurement result obtained by said aberration measurement unit.

15. A non-transitory computer-readable storage medium storing a program for causing a computer to execute a fundus imaging method defined in claim 1.

16. The method according to claim 1, wherein N=1, M=4, and L=6.

* * * * *